(12) United States Patent
Betley et al.

(10) Patent No.: US 7,998,960 B2
(45) Date of Patent: Aug. 16, 2011

(54) AFFINITY ADSORBENTS FOR PLASMINOGEN

(75) Inventors: Jason Richard Betley, Herts (GB); James Christopher Pearson, Cambridge (GB); Claudia Hildegard Kuhn, Cambridge (GB); Baldev Singh Baines, Cambridge (GB)

(73) Assignee: Prometic Biosciences Ltd., Ballasalla (IM)

( * ) Notice: Subject to any disclaimer, the term of this patent is extended or adjusted under 35 U.S.C. 154(b) by 0 days.

(21) Appl. No.: 11/913,514

(22) PCT Filed: May 9, 2006

(86) PCT No.: PCT/GB2006/001686
§ 371 (c)(1),
(2), (4) Date: Jul. 3, 2008

(87) PCT Pub. No.: WO2006/120423
PCT Pub. Date: Nov. 16, 2006

(65) Prior Publication Data
US 2008/0293925 A1    Nov. 27, 2008

(30) Foreign Application Priority Data

May 9, 2005 (GB) .................................. 0509438.8

(51) Int. Cl.
*A01N 43/66* (2006.01)
*C07H 19/12* (2006.01)
*C07K 16/06* (2006.01)
*A61K 39/395* (2006.01)

(52) U.S. Cl. ..... 514/246; 536/28.3; 530/413; 424/145.1
(58) Field of Classification Search .................. None
See application file for complete search history.

(56) References Cited

U.S. PATENT DOCUMENTS
2002/0192794 A1    12/2002 Dadd et al.

FOREIGN PATENT DOCUMENTS
| WO | WO 00/67900 | * 11/2000 |
| WO | WO-00/67900 | * 11/2000 |
| WO | WO 00/67900 A1 | 11/2000 |

OTHER PUBLICATIONS

Lowe, Christopher R. (2001) "Combinatorial approaches to affinity chromatography" *Current Opinion in Chemical Biology* 5:248-256.

* cited by examiner

*Primary Examiner* — Cecilia Tsang
*Assistant Examiner* — Satyanarayana Gudibande
(74) *Attorney, Agent, or Firm* — Saliwanchik, Lloyd & Eisenschenk

(57) ABSTRACT

For the separation, removal, isolation, purification, characterization, identification or quantification of plasminogen or a protein that is a plasminogen analogue, an affinity adsorbent is used that is a compound of formula (II) wherein one X is N and the other is N, C—Cl or C—CN; A is a support matrix, optionally linked to the triazine ring by a spacer; Z is O, S or N—R and R is H, $C_{1-6}$ alkyl, $C_{1-6}$ hydroxyalkyl, benzyl or &bgr;-phenylethyl; B is an optionally substituted hydrocarbon linkage containing from 1 to 10 carbon atoms; D is H, OH or a primary amino, secondary amino, tertiary amino, quaternary ammonium, imidazole, guanidino or amidino group; or B-D is —CHCOOH—$(CH_2)_{3-4}$—$NH_2$; and q is 2 to 6.

7 Claims, No Drawings

AFFINITY ADSORBENTS FOR PLASMINOGEN

This application is a National Stage Application of International Application Number PCT/GB2006/001686, filed May 9, 2006; which claims priority to Great Britain Application No. 0509438.8, filed May 9, 2005.

FIELD OF THE INVENTION

This invention relates to compounds and their use as affinity ligands.

BACKGROUND OF THE INVENTION

Plasminogen (alternatively known as microplasmin, PLG or angiostatin) is a single chain 91 kDa glycoprotein zymogen, and is the precursor of the fibrinolytic enzyme plasmin. The native form of plasminogen is composed of 791 amino acids with glutamic acid located at the N-terminal portion (Glu-plasminogen). Plasminogen has five homologous regions known as kringles. These regions are specific for the complimentary kringles located on tPA, uPA and prothrombin. These kringles have one high affinity and four low affinity lysine binding sites that mediate the interactions of plasminogen with fibrin and alpha-2-antiplasmin.

Plasminogen is converted to plasmin via a cascade of various reactions that result in the hydrolysis of the Arg560-Val561 peptide bond of plasminogen, resulting in two chains which remain covalently associated by a disulfide bond. The main role of the trypsin-like protease plasmin is the breakdown of clots.

Plasminogen deficiencies resulting from homo- or heterozygous mutations in the coding DNA manifest themselves in a number of pathologies, including ligneous conjunctivitis and thrombosis.

Plasminogen is present in human plasma at a concentration of ~100 μg/mL. It is possible to purify the plasminogen from plasma using immobilised lysine on a solid support, in an affinity chromatography process that is well characterised. Immobilised lysine chromatography is also used for the primary capture from cell culture harvest of proteins such as tissue plasminogen activator (tPA), commonly used as a clot-busting drug. The binding capacities of commercially available resins for plasminogen are typically in the range 0.6-1.0 mg protein/mL of adsorbent. The purity of the plasminogen eluted from these materials is excellent, with purity routinely >95% from primary capture. It would be useful to have a material retaining these characteristics of excellent elution purity, but displaying a binding capacity in excess of those currently available.

WO97/10887 discloses triazine-based compounds, useful as affinity adsorbents, of formula I

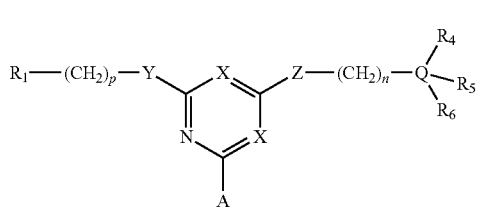

wherein $R_1$ is H, alkyl, hydroxyalkyl, cyclohexyl, $NH_2$, phenyl, naphthyl, 1-phenylpyrazole, indazole, benzthiazole, benzoxazole or benzimidazole, any of which aromatic groups can be substituted with one or more of alkyl, alkoxy, acyloxy, acylamino, amino, $NH_2$, OH, $CO_2H$, sulphonyl, carbamoyl, sulphamoyl, alkylsulphonyl and halogen;

one X is N and the other is N, C—Cl or C—CN;
Y is O, S or $NR_2$;
Z is O, S or $NR_3$;
$R_2$ and $R_3$ are each H, alkyl, hydroxyalkyl, benzyl or β-phenylethyl;
Q is benzene, naphthalene, benzthiazole, benzoxazole, 1-phenylpyrazole, indazole or benzimidazole;
$R_4$, $R_5$ and $R_6$ are each H, OH, alkyl, alkoxy, amino, $NH_2$, acyloxy, acylamino, $CO_2H$, sulphonic acid, carbamoyl, sulphamoyl, alkylsulphonyl or halogen;
n is 0 to 6;
p is 0 to 20; and
A is a support matrix, optionally linked to the triazine ring by a spacer.

Compounds of formula I are disclosed as having affinity for proteins such as immunoglobulins, insulin, Factor VII or human growth hormone.

Compounds of related structure are disclosed in WO00/67900 and WO03/097112. They have affinity for endotoxins.

SUMMARY OF THE INVENTION

Surprisingly, it has been found that certain compounds, many of which are novel, are useful for affinity-based isolation of plasminogen. These compounds are of formula II

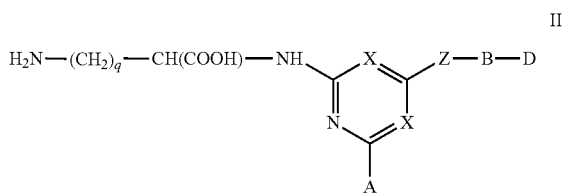

wherein A, X and Z are as defined for formula I above;
B is an optionally substituted hydrocarbon linkage containing from 1 to 10 carbon atoms;
D is H, OH or a primary amino, secondary amino, tertiary amino, quaternary ammonium, imidazole, guanidino or amidino group; or
B-D is —CHCOOH—$(CH_2)_{3-4}$—$NH_2$; and
q is 2 to 6.

Further, compounds of the invention include the corresponding ligands, in which A is replaced by a functional group, linked directly or indirectly to the triazine ring, which can be reacted so that the compound is immobilised on a support matrix. The terms "ligand" and "adsorbent" may be used interchangeably, below.

DESCRIPTION OF THE INVENTION

WO97/10887, WO00/67900 and WO03/097112 disclose how combinatorial libraries of ligands can be built on a solid support. Their disclosures, including examples of embodiments and procedures common to the present invention, are incorporated herein by reference. During the screening of a set of these combinatorial libraries with pooled human plasma as feedstock, a number of ligands were identified as being capable of selectively binding and eluting human plasminogen.

Compounds of formula II, for use in the invention, can be prepared by procedures known to those skilled in the art. Such procedures are described in the 3 PCT publications identified above; they can be readily adapted to the preparation of new compounds.

In compounds of the invention, q is preferably 4. It will be appreciated that this "arm" of the molecule is derived from lysine. B preferably includes an aromatic, e.g. benzene, ring.

WO97/10887 gives examples of A, including spacers or linkers L via which the triazine ring may be linked to a solid support M. As described in WO97/10887, such supports include agarose, silica, cellulose, dextran, starch, alginate, carrageenan, synthetic polymers, glass and metal oxides. Such materials may be activated before reaction to form an adsorbent of this invention.

L may be, for example, -T-$(-V^1-V^2)_m-$, wherein
T is O, S or $-NR^7-$;
m is 0 or 1;
$V^1$ is an optionally substituted hydrocarbon radical of 2 to 20 C atoms; and
$V^2$ is O, S, $-COO-$, $-CONH-$, $-NHCO-$, $-PO_3H-$, $-NH$-arylene-$SO_2-CH_2-CH_2-$ or $-NR_8-$; and
$R^7$ and $R^8$ are each independently H or $C_{1-6}$ alkyl.

In a preferred embodiment of the invention, the plasminogen-binding adsorbent is represented by structure III

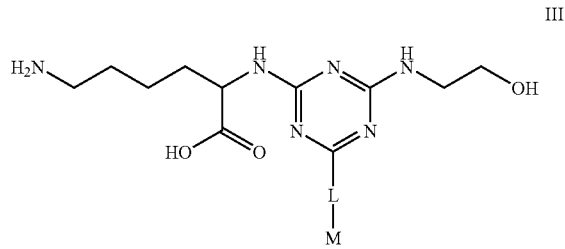

III

In a further preferred embodiment of the invention, the plasminogen-binding adsorbent is represented by structure IV

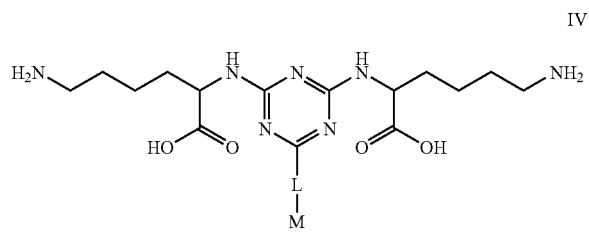

IV

In a further preferred embodiment of the invention, the plasminogen-binding adsorbent is represented by structure V

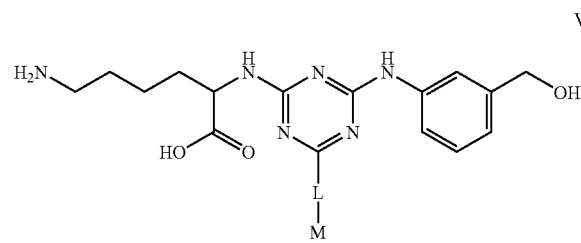

V

The plasminogen-binding ligands and adsorbents described herein are useful for the affinity isolation and purification of plasminogen from various fluids and complex mixtures including, but not limited to, human plasma, human plasma depleted of one or more other proteins and recombinant fermentation supernatants. This utility is demonstrated below in Example 4, by chromatography experiments using human pooled plasma.

The term "plasminogen" is used herein to describe plasminogen itself and also analogues that have the functional characteristics of plasminogen, e.g. in terms of affinity to a given compound described herein. Thus, the analyte may be a protein that is a functional fragment of plasminogen, or a structural analogue having one, more of all of the same binding sites, or a fusion protein.

The following Examples illustrate the invention.

EXAMPLE 1

Synthesis of Adsorbent III

6% cross-linked Purabead agarose gel (1000 g settled in Reverse Osmosis (RO) water) was slurried with RO water (670 mL), 10 M sodium hydroxide (NaOH) (90 mL), and epichlorohydrin (127 mL). The slurry was stirred over 2 hours. After a sample was taken for analysis, the slurry was filtered, then washed with RO water (12×1 L). Analysis for epoxy groups showed that the gel was derivatised with 17.3 μmol epoxy groups per g of settled gel.

The gel was drained before RO water (800 mL) and 0.88 specific gravity aqueous ammonia solution (200 mL) were added. The mixture was stirred and heated to 40° C., then stirred at this temperature over 16 hours. After a sample was taken for analysis, the slurry was filtered, then washed with RO water (12×1000 mL). TNBS analysis for amine groups showed that the gel was derivatised with 25.6 μmol amine groups per g of settled gel.

The settled, aminated gel (1000 g) was suspended in 1 M potassium phosphate pH 7.0 (1 L), then allowed to drain. To this gel was then added 1 M potassium phosphate pH 7.0 (250 mL), and RO water (250 mL). The slurry was stirred vigorously while acetone (500 mL) was added. After cooling in an ice/salt bath over 30 minutes, cyanuric chloride (25 g) in cold acetone (250 mL) was added in one portion. The mixture was stirred at 0° C. over 1 hour, before being washed with 50% aqueous acetone (5×1 L), RO water (5×1 L), 50% aqueous acetone (5×1 L), and RO water (10×1 L). The gel was allowed to settle under gravity, before a sample was taken for analysis. Analysis for chloride release indicated that the gel was derivatised with 16.8 μmol substituted dichlorotriazine per g of settled gel.

Settled gel from the previous stage (1000 g) was slurried with 1 M potassium phosphate buffer (1 L) containing lysine hydrochloride (45 g), pH 8.5, at room temperature over 16 hours. The slurry was filtered, then washed with RO water (15×1 L). To 950 g (settled) of the gel slurried in RO water (950 mL) was added ethanolamine (14.82 g). The mixture was stirred at 60° C. overnight. After a sample of the supernatant was taken for analysis, the slurry was filtered, then washed with RO water (12×1 L). Analysis for chloride release indicated that the gel had been derivatised with 22.7 μmol ethanolamine per g of settled gel.

The gel was incubated in a final concentration of 0.5 M NaOH overnight at 40° C., then washed with 0.5 M NaOH (5×1 L). After the final wash was allowed to drain under gravity, 0.5 M NaOH (1 L) was added and the mixture incubated at 40° C. overnight. The gel was then washed with 0.5 M NaOH (5×1 L), then RO water (10×1 L). After washing with 0.1 M PBS pH 7.0 (3×1 L), the gel was washed a further time with RO water (10×1 L), before storage in the cold room at 4° C. in 20% v/v aqueous ethanol.

EXAMPLE 2

Synthesis of Adsorbent IV

Dichlorotriazine-activated agarose was prepared according to the method described in Example 1. Settled gel (41.5 g, 22 µmol DCT/g settled) was reacted overnight at 60° C. with an aqueous solution of lysine hydrochloride (1.67 g, 10 molar equivalents) in water (40 mL) while maintaining the pH at 9.0 with 10 M NaOH. At this point the gel was washed with 50% aqueous dimethyl formamide (5×80 mL), RO water (5×80 mL), 0.1 M HCl (5×80 mL), 30% isopropanol/0.2 M NaOH (5×80 mL), and RO water (5×80 mL), before storage in the cold room at 4° C. in 20% v/v aqueous ethanol.

EXAMPLE 3

Synthesis of Adsorbent V

Dichlorotriazine-activated agarose was prepared according to the method described in Example 1. Settled gel (43 g, 21.1 µmol DCT/g settled) was reacted for 30 minutes at 5° C. with a solution of 2-(hydroxymethyl)aniline (0.56 g, 5 molar equivalents) in 50% DMF/water (40 mL). At this point the gel was washed with 50% aqueous dimethyl formamide (5×80 mL), and RO water (5×80 mL). The gel was then reacted overnight at 60° C. with an aqueous solution of lysine hydrochloride (1.71 g, 10 molar equivalents) in water (40 mL) while maintaining the pH at 9.0 with 10 M NaOH. At this point the gel was washed with 50% aqueous dimethyl formamide (5×80 mL), RO water (5×80 mL), 0.1 M HCl (5×80 mL), 30% isopropanol/0.2 M NaOH (5×80 mL), and RO water (5×80 mL), before storage in the cold room at 4° C. in 20% v/v aqueous ethanol.

EXAMPLE 4

Chromatography with Adsorbents III, IV and V Using Human Plasma

Chromatography experiments were performed using a 1.6 cm internal diameter, 10 cm bed height column chromatography column using an Akta Explorer chromatography system. The column was equilibrated with 140 mM sodium chloride/20 mM sodium citrate/20 mM Tris pH 7.5 at 100 cm/hr. Human plasma (Adjusted to 20 mM Tris/pH 7.5 filtered through 3, 0.8, 0.45, and 0.2 µm filters, 1.3 L) was then loaded at 50 cm/hr. Post-load wash was with 140 mM sodium chloride/20 mM sodium citrate/20 mM Tris pH 7.5 at 50 cm/hr to baseline absorbance. The column was then eluted with 140 mM sodium chloride/20 mM sodium citrate/20 mM Tris/500 mM ε-aminocaproic acid, pH 7.5 at 100 cm/hr, and regenerated with 0.5 M sodium hydroxide. Load, non-bound, and elution fractions were analysed by nephelometry to determine binding capacities. SDS PAGE was carried out to determine purity.

The purity of elution fractions from all of the adsorbents was >85%. Dynamic binding capacities (at 10% breakthrough) are shown in Table 1.

TABLE 1

| Adsorbent | Dynamic Binding Capacity (mg/mL) |
| --- | --- |
| III | 4.75 |
| IV | 4.0 |
| V | 17.0 |

The invention claimed is:

1. A method for purifying plasminogen or a protein that is a plasminogen analogue, wherein said method comprises contacting a sample containing plasminogen or a plasminogen analogue with an affinity adsorbent of formula II

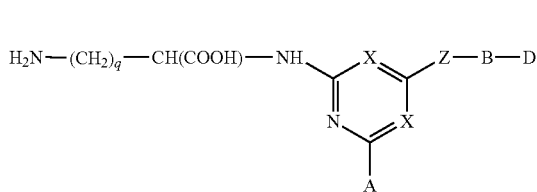

wherein one X is N and the other X is N, C—Cl or C—CN;
  A is a support matrix, optionally linked to the triazine ring by a spacer;
  Z is O, S or N—R and R is H, $C_{1-6}$ alkyl, $C_{1-6}$ hydroxyalkyl, benzyl or β-phenylethyl;
  B is an optionally substituted hydrocarbon linkage containing from 1 to 10 carbon atoms;
  D is OH or a primary amino; and
  q is 2 to 6;
whereby plasminogen or a plasminogen analogue present in the sample binds to the affinity adsorbent of formula II and wherein said method further comprises removing the plasminogen, or analogue thereof, from the affinity adsorbent to obtain plasminogen, or analogue thereof, of greater than 85% purity.

2. The method, according to claim 1, wherein the adsorbent is of formula III:

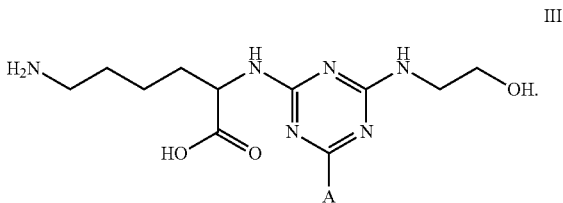

3. The method, according to claim 1, wherein the adsorbent is of formula V:

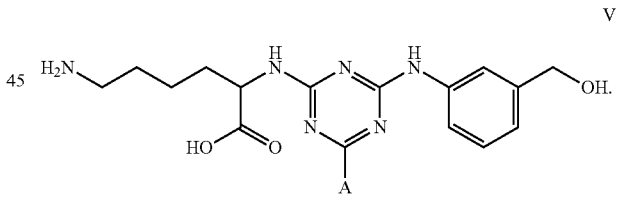

4. The method, according to claim 1, wherein the plasminogen is in a sample of plasma.

5. The method, according to claim 1, wherein said affinity adsorbent is a compound of formula II

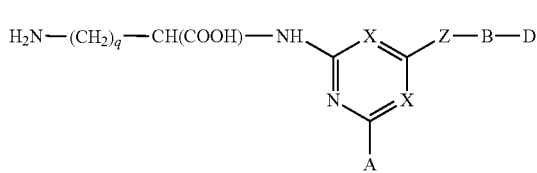

wherein one X is N and the other X is N, C—Cl or C—CN;
  A is a support matrix, optionally linked to the triazine ring by a spacer;

Z is NH;
B is a hydrocarbon linkage containing from 1 to 10 carbon atoms;
D is OH; and
q is 2 to 6.
6. The method, according to claim 1, wherein the affinity adsorbent is contacted with a sample of plasma.
7. The method, according to claim 1, wherein the adsorbent is of formula. IV:
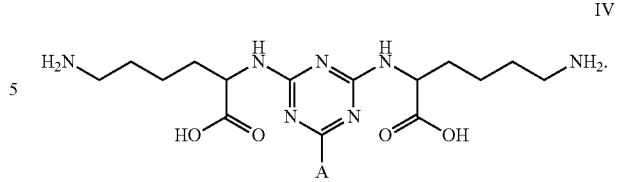
* * * * *

UNITED STATES PATENT AND TRADEMARK OFFICE
CERTIFICATE OF CORRECTION

| | | |
|---|---|---|
| PATENT NO. | : 7,998,960 B2 | Page 1 of 1 |
| APPLICATION NO. | : 11/913514 | |
| DATED | : August 16, 2011 | |
| INVENTOR(S) | : Jason Richard Betley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

This patent is subject to a terminal disclaimer(s). --

Signed and Sealed this
Twentieth Day of December, 2011

David J. Kappos
*Director of the United States Patent and Trademark Office*